United States Patent
Tsuchiya et al.

(10) Patent No.: US 7,201,891 B1
(45) Date of Patent: Apr. 10, 2007

(54) PHARMACEUTICAL PREPARATION FOR THE DIAGNOSIS OF HELICOBACTER PYLORI INFECTION

(75) Inventors: Kyoko Tsuchiya, Tokyo-to (JP); Akio Okamura, Tokushima-ken (JP); Junichi Kawasaki, Tokushima-ken (JP); Shinichiro Uno, Yokohama (JP); Atsunari Noda, Tokushima-ken (JP); Satoshi Nishiwaki, Tokushima-ken (JP)

(73) Assignee: Otsuka Pharmaceutical Co., Ltd., Tokyo-To (JP)

( * ) Notice: Subject to any disclaimer, the term of this patent is extended or adjusted under 35 U.S.C. 154(b) by 0 days.

(21) Appl. No.: 09/650,749

(22) Filed: Aug. 30, 2000

(30) Foreign Application Priority Data

May 19, 2000 (JP) .............................. 2000-148150

(51) Int. Cl.
*A61B 5/055* (2006.01)
(52) U.S. Cl. ..................... 424/9.3; 424/1.29; 424/1.33; 424/1.25; 424/9.1
(58) Field of Classification Search ............... 424/1.29, 424/1.37, 1.81, 1.65, 474, 475
See application file for complete search history.

(56) References Cited

U.S. PATENT DOCUMENTS

| | | | | |
|---|---|---|---|---|
| 4,709,095 A | * | 11/1987 | Yamanaka et al. | 564/253 |
| 5,662,935 A | * | 9/1997 | Motta | 424/465 |
| 5,848,975 A | * | 12/1998 | Phillips | 600/532 |
| 6,067,989 A | * | 5/2000 | Katzman | 128/898 |
| 6,113,875 A | * | 9/2000 | Nystrom et al. | 424/1.29 |
| 6,171,811 B1 | * | 1/2001 | Becerro De Bengoa Vallejo | 435/34 |
| 6,180,414 B1 | * | 1/2001 | Katzman | 436/181 |
| 6,180,636 B1 | * | 1/2001 | Traxler et al. | 514/258 |
| 6,187,340 B1 | * | 2/2001 | Fukuta et al. | 424/474 |
| 6,194,000 B1 | * | 2/2001 | Smith et al. | 424/458 |
| 6,294,151 B1 | * | 9/2001 | Hayakawa et al. | 424/1.81 |

FOREIGN PATENT DOCUMENTS

| | | |
|---|---|---|
| EP | 0860170 A | 8/1998 |
| EP | 0 878 198 A1 | 11/1998 |
| JP | 6-157317 | 6/1994 |
| WO | 96/14091 | 5/1996 |
| WO | WO 98/53808 A | 12/1998 |

OTHER PUBLICATIONS

Supplementary European Search Report issued in Applicaiton No. 01930187.8-2107, PCT/JP0104122, dated Feb. 6, 2006.

\* cited by examiner

*Primary Examiner*—Sreenivasan Padmanabhan
*Assistant Examiner*—Leonard Williams
(74) *Attorney, Agent, or Firm*—Finnegan, Henderson, Farabow, Garrett & Dunner, L.L.P.

(57) ABSTRACT

A coated preparation for the detection of a *H. pylori* infection according to a urea breath test protocol which comprises a core composition containing at least an isotope C-labeled urea, an excipient and a lubricant in defined proportions and covered with 0.1~10 weight % of a coating agent based on 100 weight % of the core composition. With this preparation, the influence of the urease-producing bacteria resident in organs other than the stomach, such as the mouth and throat, is excluded to enable a diagnosis of *H. pylori* infection without the risk for a false-positive test and with reasonable rapidity.

15 Claims, 1 Drawing Sheet

PHARMACEUTICAL PREPARATION FOR THE DIAGNOSIS OF HELICOBACTER PYLORI INFECTION

FIELD OF THE INVENTION

The present invention relates to a pharmaceutical preparation for use in the diagnosis of *Helicobacter pylori* infection. More particularly, the invention relates to an oral dosage form which finds application in urea breath testing which is a noninvasive method of detecting *Helicobacter pylori*.

DESCRIPTION OF RELATED ART

Since the successful isolation and culture of *Helicobacter pylori* (hereinafter referred to as *H. pylori*) by Marshall et al. (Lancet, pp. 1273–1275 (1983)), both affirmative and negative views had been advanced on its etiologic role. Recently, however, *H. pylori* infection has gathered a great deal of attention as a principal cause or a cofactor in the onset of gastritis, peptic ulcer and stomach cancer which are the triad of major upper digestive tract diseases not only in Japan but also abroad. In particular, the recommendation made by NIH Consensus Conference (Bethesda, 1994) that "Peptic ulcer in which an *H. pylori* infection has been verified, whether it is a primary lesion or a recurrent one, requires eradication therapy supplementing gastric acid antisecretary medication with antibacterials" caused quite a sensation in Japan, urging those concerned to establish an accurate and rapid method for diagnosis of *H. pylori* infection and verification of eradication of *H. pylori*.

The technology for detecting *H. pylori* in the gastric mucosa can be divided into two major categories, namely the invasive one requiring an endoscopy (biopsy) (a bacteriological method involving culture of isolates, a histologic or immunohistologic method for detection, urease test, etc.) and the noninvasive one. Of them, the noninvasive one is preferred from the standpoints of mental and physical burdens on the patient, expediency and safety.

The two representative noninvasive methods currently available are a serologic method for diagnosis which comprises determining the serum level of specific anti-*H. pylori* antibodies and the urea breath test which comprises administering an isotope carbon-labeled urea orally and determining the labeled carbon dioxide expired in breath air (e.g. Sand, J., Gastroenterol, 1996, 31 (suppl) 214, pp. 44–46; Gastraenteralogy, 1997, 113, s93–98; Gut, 1994, 35, pp. 723–725; Aliment. Pharmacol. Ther. 1997, 11, pp. 641–649; Gastraenteralogy, 1995, 109, pp. 136–141).

Between the above methods, the serologic method for diagnosis which is based on the presence of specific antibodies has the drawback that since the antibody-positive status of the host's serum persists for at least 3 months even after eradication of *H. pylori*, approximately 10~15% of the test subjects give false-positive responses and, as such, is not suited for the confirmation of bacterial elimination. Therefore, recently the urea breath test, which is not dependent on the presence of antibodies and is safe and not time-consuming, is broadly employed. This test is based on the property of *H. pylori* to produce a large amount of the enzyme urease. The urease usually dose not occur in the human body and, therefore, its detection indicates that *H. pylori*, an urease producer, exists in the stomach. Thus, this method exploits the phenomenon that when the urease-producer *H. pylori* exists in the host's stomach, the labeled urea ingested by the host decomposes and further reacts with gastric acid so that the labeled urea is converted to the labeled carbon dioxide which is expired in breath air (Lancet, pp. 174–177 (1987)). A further advantage of this test is that the existence of urease can be tested in a broad region of the stomach.

However, the conventional procedure for this urea breath test involves the intake of an isotope-labeled urea in the form of an aqueous solution and, therefore, various urease-producing bacteria resident in the mouth and throat decompose the ingested urea in an early stage following administration, thus presenting a risk for giving a false-positive test in the diagnosis of *H. pylori* infection. To prevent this false-positive response, it is necessary to have the test subject gargle his throat with water immediately following ingestion of an aqueous solution of the labeled urea to wash away the labeled urea remaining in the oral cavity or to disinfect the mouth and throat ahead of time.

However, such treatments are burdensome not only to test subjects undergoing the test but also to the physician. Moreover, in order to obtain an accurate result, the detection noise due to the decomposition of urea by the resident bacterial flora in and around the oral cavity must be eliminated by delaying the expired air collection time, with the consequent disadvantage of a prolongation of the test procedure.

SUMMARY OF THE INVENTION

The present invention has for its object to provide an improved oral formulation for a urea breath test. More, particularly, the object of the invention is to provide a pharmaceutical preparation with which an *H. pylori* infection of the gastric mucosa can be detected and diagnosed expediently and noninvasively by the urea breath test and which is free from the risk for a false positive test because of complete elimination of the influence of urease-producing bacteria inhabiting the oral cavity, throat and other tissues expecting the gastrointestinal tract.

A further object of the present invention is to provide a pharmaceutical preparation with which the presence of *H. pylori* can be detected quickly without a time lag.

To overcome the foregoing disadvantages of the conventional urea breath test, the invent rs of the present invention explored in earnest for the development of a pharmaceutical formulation which would show an in vivo behavior such that it remains undissolved in the oral cavity but, upon entry into the stomach, dissolves quickly to allow the labeled urea to disperse rapidly throughout the stomach. As a result, they discovered that a pharmaceutical formulation showing such a favorable in vivo behavior can be provided by using the active substance labeled urea in combination with an excipient component and a lubricant component to prepare a core composition and covering this core composition with a coating agent. Thus, the inventors confirmed that when the above pharmaceutical preparation is administered orally to a test subject, the active substance reaches the stomach without being affected by the urease-producing bacteria resident in the oral cavity and is rapidly dissolved and dispersed in the stomach substantially without being subjected to the retardation of dissolution by the coating and that, therefore, this pharmaceutical preparation is a very useful reagent for the rapid and accurate diagnosis of *H. pylori* infection. The present invention has been completed on the basis of the above finding.

The present invention, therefore, is concerned with the pharmaceutical preparations defined in the following paragraphs (1)~(14) for the detection of *H. pylori* infection according to a urea breath test protocol:

(1) A coated preparation for use in the detection of *H. pylori* infection according to a urea breath test protocol, comprising a core composition coated with 0.1~10 weight % of a coating agent based on 100 weight % of said core composition, said core composition comprising 19~89 weight % of isotope carbon-labeled urea, 10~80 weight % of an excipient component and 0.01~1 weight % of a lubricant component based on 100 weight % of the core composition.

(2) A coated preparation as defined in paragraph (1) wherein the amount of the coating agent is 0.3~5 weight % based on 100 weight % of the core composition.

(3) A coated preparation as defined in paragraph (1) wherein the amount of the coating agent is 0.5~3 weight % based on 100 weight % of the core composition.

(4) A coated preparation as defined in paragraph (1) containing 25~75 weight % of the isotope carbon-labeled urea, 20~70 weight % of the excipient component and 0.05~0.8 weight % of the lubricant component based on 100 weight % of the core composition.

(5) A coated preparation as defined in paragraph (1) containing 30~70 weight % of the isotope carbon-labeled urea, 35~65 weight % of the excipient component and 0.1~0.7 weight % of the lubricant component based on 100 weight % of the core composition.

(6) A coated composition as defined in paragraph (1) wherein the core composition contains 10~450 weight % of the excipient component and 0.01~6 weight % of the lubricant component based on 100 weight % of the isotope carbon-labeled urea.

(7) A coated preparation as defined in paragraph (1) wherein the core composition contains 50~150 weight % of the excipient component and 0.1~5 weight % of the lubricant component based on 100 weight % of the isotope carbon-labeled urea.

(8) A coated preparation as defined in paragraph (1) wherein the coating agent comprises a water-soluble polymer and a plasticizer.

(9) A coated preparation as defined in paragraph (8) wherein the water-soluble polymer is at least one member selected from the group consisting of pullulan, dextrin, alkali metal alginate, hydroxypropylcellulose, hydroxypropylmethylcellulose, methylcellulose and polyvinylpyrrolidone.

(10) A coated preparation as defined in paragraph (8) wherein the plasticizer is at least one member selected from the group consisting of polyvinyl alcohol, polyethylene glycol, triethyl citrate, triacetin, concentrated glycerin, propylene glycol and polysorbate.

(11) A coated preparation as defined in paragraph (1) wherein, as the excipient component, the core composition contains at least one member selected from the group consisting of lactose, sucrose, glucose, starch, crystalline cellulose, croscarmellose sodium, low-substitution hydroxypropylcellulose, carmellose calcium, crospovidone, carboxymethylstarch sodium, carboxymethylstarch calcium, hydroxypropylstarch, polyvinylpyrrolidone and partly pregelatinized starch.

(12) A coated preparation as defined in paragraph (1) wherein, as the lubricant component, the core composition contains at least one member selected from the group consisting of stearic acid, magnesium stearate, calcium stearate and hydrogenated oil.

(13) A coated preparation as defined in paragraph (1) wherein the core composition contains lactose, crystalline cellulose and starch as the excipient component and magnesium stearate as the lubricant component and the coating agent contains hydroxypropylmethylcellulose, polyethylene glycol, titanium oxide and talc.

(14) A coated preparation as defined in paragraph (1) wherein the isotope carbon-labeled urea is $^{13}$C-labeled urea.

The present invention is further concerned with a method defined in the following paragraph (15) or (16) for detecting *H. pylori* infection using any of the above-defined coated preparations:

(15) A method of detecting a *H. pylori* infection comprising using the coated preparation defined in paragraph (1) as a urea breath test reagent.

(16) A method of detecting a *H. pylori* infection which comprises a step of administering the coated preparation defined in paragraph (1) to a test subject, a step of collecting expired air after a given time period, and a step of measuring the ratio of the isotope carbon-labeled $CO_2$ to $^{12}CO_2$ in the expired air.

The present invention is further concerned with a method for assessment of *H. pylori* eradication effect which comprises using any of the above-defined coated preparations, the procedure of which method may for example comprise a step of administering the coated preparation defined in any of paragraphs (1) through (14) to a patient on *H. pylori* eradication therapy, a step of collecting expired air after a given time period, and a step of determining the ratio of the isotope carbon-labeled $CO_2$ to $^{12}CO_2$ in the expired air.

DETAILED DESCRIPTION OF THE INVENTION

Figure 1:
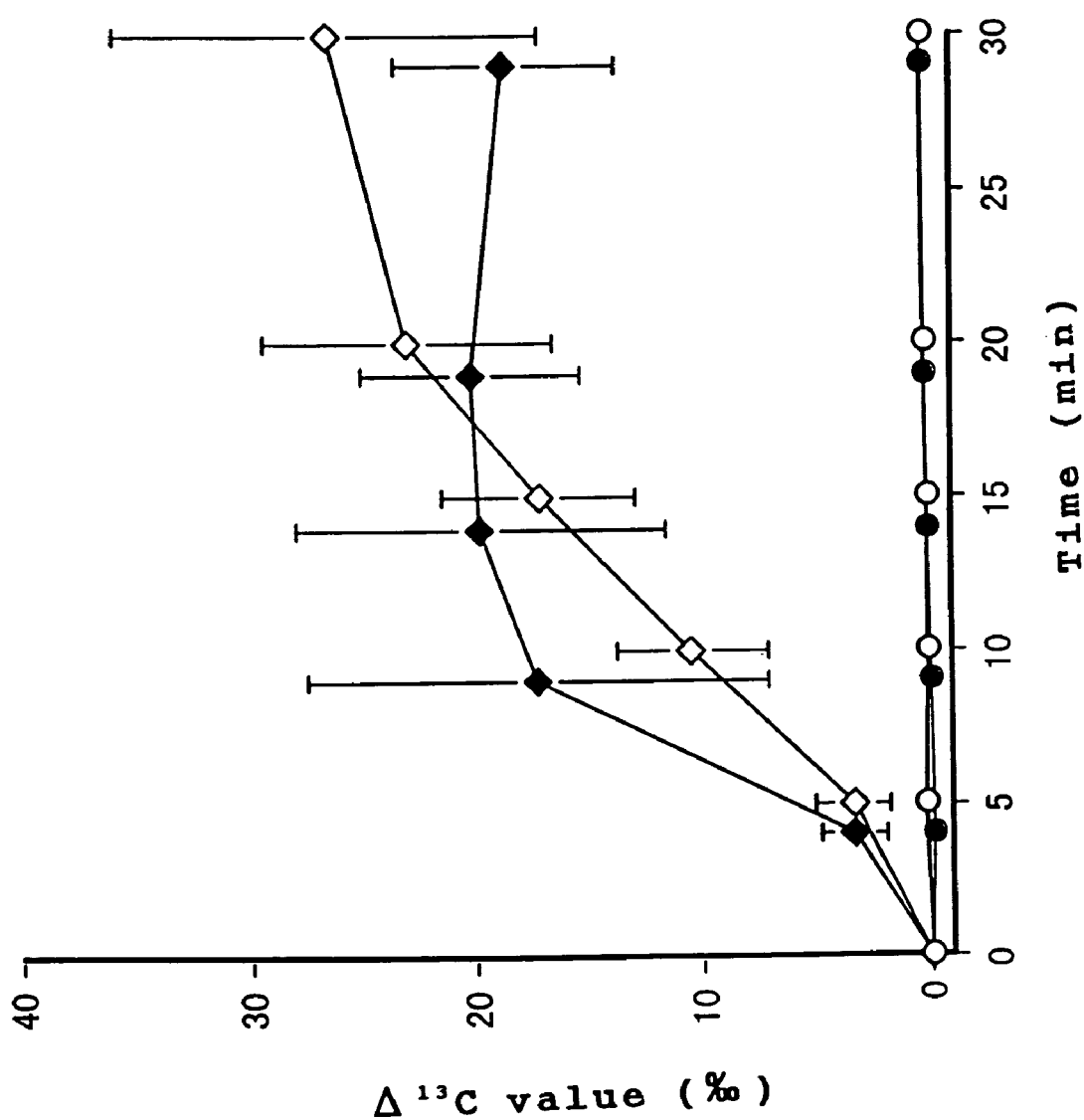
FIG. 1 shows the results of Example 3 in which the $^{13}$C-labeled urea tablet (coating 2 weight %) was administered orally to test groups (a mouth-washed group and a non-mouth-washed group each consisting of *H. pylori*-negative and -positive subjects) and the time course of Δ $^{13}$C value (‰) (the difference in the $^{13}CO_2/^{12}CO_2$ concentration ratio (δ $^{13}$C value) in expired air between the expired air before and after medication) was monitored. In the diagram, the closed circle represents *H. pylori*-negative cases (in mouth-washed group), the open circle represents *H. pylori*-negative cases (in the non-mouth-washed group), the closed diamond represents *H. pylori*-positive cases (in the mouth-washed group), and the open diamond represents *H. pylori*-positive cases (in the non-mouth-washed group). Each graph shows the mean ± standard error for the total test population.

The pharmaceutical preparation according to the present invention is a preparation for use in the detection of *H. pylori* infection by urea breath testing, characterized in that said preparation is a coated preparation comprising a core composition containing an active component and a coating material covering the core composition.

Furthermore, the core composition constituting the coated preparation of the present invention is characterized in that, in addition to the active component isotope carbon-labeled urea (hereinafter referred to as the isotope C-labeled urea), the preparation contains an excipient component and a lubricant component each in a herein-defined proportion.

The isotope C-labeled urea for use in the practice of the present invention is urea labeled with an isotope of carbon and serves as an active component for detection of *H. pylori* infection. As isotopes of carbon, the stable isotope $^{13}$C and the radioactive isotope $^{11}$C or $^{14}$C can be generally mentioned, and as urea labeled by the respective isotopes, $^{13}$C-labeled urea and $^{11}$C-labeled urea or $^{14}$C-labeled urea can be mentioned. These species of labeled urea are invariably used in urea breath tests and all can be used in the present invention as well in the routine manner. Preferably, $^{13}$C-labeled urea, i.e. urea labeled with the highly stable isotope $^{13}$C, is used as said isotope C-labeled urea.

The formulating amount of said isotope C-labeled urea in the core composition is not particularly restricted inasmuch as it is within the range of 19~89 weight % per 100 weight % of the core composition. The preferred proportion is 25~75 weight % and the more preferred proportion is 30~70 weight %.

As the excipient component, the various excipients which are in routine use in the production of pharmaceutical preparati ns, particularly those in use as excipients for tablets, can be liberally used in the present invention as well. Specifically, there can be mentioned saccharides such as lactose, sucrose, glucose, etc.; water-soluble or water-swellable cellulose derivatives such as crystalline cellulose, low-substitution hydroxypropylcellulose, carboxymethylcellulose calcium (carmellose calcium), croscarmellose sodium, etc.; starch or starch derivatives such as starch, carboxymethylstarch sodium, hydroxypropylstarch, partly pregelatinized starch, etc.; and vinylpyrrolidone derivatives inclusive of polyvinylpyrrolidones such as crospovidone; among others. These may be used each independently or in a suitable combination of two or more species. The preferred excipients are lactose, crystalline cellulose and starch, and it is preferable to use at least two of them in combination. The mode of combination is not particularly restricted but includes the combination of lactose with either crystalline cellulose or starch, the combination of crystalline cellulose with starch, and the combination of lactose with crystalline cellulose and starch.

The formulating amount of the excipient component in the core composition is not particularly restricted inasmuch as it is within the range of 10~80 weight % but preferably is 20~70 weight %, more preferably 35~65 weight % based on 100 weight % of the core composition. It is also recommended that the formulating amount of said excipient component based on 100 weight % of isotope C-labeled urea should be generally 10~450 weight %, preferably 50~150 weight %.

With regard to the lubricant component, the various lubricants in routine use in the manufacture of pharmaceutical products, particularly those used as lubricants for tablets, can be liberally employed. Specifically, stearic acid, magnesium stearate, calcium stearate, hydrogenated oil, etc. can be mentioned by way of example. These may be used each independently or in a suitable combination of two or more species. The preferred lubricant is magnesium stearate.

The formulating amount of said lubricant component in the core composition is not particularly restricted inasmuch as it is within the range of 0.01~1 weight % but is preferably 0.05~0.8 weight %, more preferably 0.1~0.7 weight %, based on 100 weight % of the core composition. Moreover, the preferred proportion of this lubricant component based on 100 weight % of isotope C-labeled urea is usually 0.01~6 weight %, preferably 0.1~5 weight %.

In addition to the above-mentioned components, the core composition for constituting the core of the coated preparation of the present invention may be supplemented with such other components as binder, foaming agent, coloring agent, flavor, corrigent, sweetener, etc. in amounts not interfering with the effect of the invention. As such additional components, the substances which are in routine use in the manufacture of pharmaceutical preparations, particularly tablets, can be liberally employed.

The coated preparation of the present invention is manufactured by using a core comprising at least said isotope C-labeled urea, said excipient component and said lubricant component [uncoated tablet (core tablet), uncoated pill, uncoated granule] and covering its surface with a coating agent.

The coating agent which can be used in the manufacture of the coated preparation of the invention is not particularly restricted but includes a broad variety of coating agents (film-forming agents) in routine use for tablets, pills, granules and so forth. The preferred is a water-soluble coating agent.

The water-soluble coating agent includes polysaccharides which may optionally have a sulfate group, such as pullulan, dextrin and alkali metal salts (e.g. sodium salt, potassium salt) of alginic acid, etc.; water-soluble cellulose derivatives such as cellulose containing 26~33% of methoxy groups, e.g. methylcellulose, and cellulose containing 53.4~77.5% or 7~12% of hydroxypropoxy groups, e.g. hydroxypropylcellulose and hydroxypropylmethylcellulose, etc.; water-soluble polyvinyl derivatives such as polyvinylpyrrolidone, polyvinyl alcohol, etc.; enteric polymers such as carboxymethylethylcellulose, hydroxypropylmethylcellulose phthalate, cellulose acetate phthalate, hydroxypropylmethylcellulose acetate succinate, methacrylic copolymer, carboxymethylethylcellulose, etc.; gastric polymers such as polyvinyl acetal diethylaminoacetate, aminoalkyl methacrylate copolymer E, etc.; and sustained-rel as polymers such as ethylcellulose etc. These may be used each alone or in a combination of two or more species.

The preferred, among these water-soluble polymers, are pullulan, dextrin, alkali metal alginate (sodium alginate, potassium alginate), hydroxypropylcellulose, hydroxypropylmethylcellulose, methylcellulose and polyvinylpyrrolidone, and the still more preferred are hydroxypropylcellulose and hydroxypropylmethylcellulose.

The coating agent for use in the present invention may be one containing only a single species of said water-soluble polymer or one containing two or more species in a suitable combination.

In the present invention, a coating agent comprising such a water-soluble polymer is preferably used in conjugation with a plasticizer. As such plasticizer, the plasticizers in routine use in coating compositions can be selectively used and specifically polyhydric alcohols such as polyethylene glycols inclusive of macrogol 6000, macrogol 4000, etc., concentrated glycerin, propylene glycol, polyvinyl alcohol, etc.; triethyl citrate; triacetin; and surfactants such as polysorbate (e.g. Tween 80) can be mentioned as examples.

These plasticizers can each be used in conjunction with said water-soluble polymer or be used in a combination of two or more in conjunction with the water-soluble polymer. As the preferred plasticizer, polyvinyl alcohol, polyethylene glycol, triethyl citrate, triacetin, concentrated glycerin, propylene glycol or polysorbate can be mentioned. Among them, polyethylene glycol is preferred and macrogol 6000 is the more preferred.

The mode of combination of said water-soluble polymer with said plasticizer is not particularly restricted but includes, to mention a few preferred examples, the combination of hydroxypropylcellulose with polyethylene glycol, triethyl citrate or triacetin and the combination of hydroxypropylmethylcellulose with polyethylene glycol, triethyl citrate or triacetin. The more preferred combination is the combination of hydroxypropylmethylcellulose with polyethylene glycol.

The coating agent for use in the present invention may be supplemented with a coloring agent such as a pigment or a dye, a flavor, a corrigent and/or a sweetener each in an amount not interfering with the operation and result of the present invention. As such formulating additives, those in routine use in pharmaceutical formulations, particularly in coating formulations, can be liberally employed. As examples of the coloring agent, titanium oxide, talc, iron oxide red, etc. can be mentioned. The preferred are titanium oxide and talc. The coloring agent is intended to impart a desired color to the coated preparation of the invention and its amount is not particularly restricted inasmuch as it is sufficient to satisfy the need. Usually, such a coloring agent is used in a proportion of 1~70 weight %, preferably 5~50 weight %, based on 100 weight % of the coating agent. When talc and titanium oxide are used in combination, their ratio in the coating agent may be 25~175 weight parts, preferably 50~150 weight parts, of talc to 100 weight parts of titanium oxide.

The amount of the coating agent to be used for covering the core composition [e.g. uncoated tablet (core tablet), uncoated pill, uncoated granule] can be judiciously selected from the range of 0.1~10 weight % based on 100 weight % of the core composition and is preferably 0.3~5 weight %, more preferably 0.5~3 weight %. If the proportion exceeds 10 weight % in a large measure, the dissolution of the coating film in the stomach is retarded to cause a marked delay in the dispersion and dissolution of the core composition, with the consequent disadvantage of frustrating a rapid diagnosis. On the other hand, if the proportion is by far smaller than 0.1 weight %, the influence of urease-producing bacteria in the mouth and throat may not be excluded so that a false-positive result tends to result.

The method of covering the core composition with said coating agent is not particularly restricted but the coating can be performed in the usual manner according to the form of the core composition or final preparation.

The form of the coated preparation of the invention is not particularly restricted inasmuch as the operation and result of the invention may be implemented, thus including tablets, pills and granules, among others. The preferred are tablets and pills, with tablets being particularly preferred. These dosage forms can be manufactured by the methods established in the art.

Taking the manufacture of tablets as an example, the coated preparation of the invention can be manufactured by preparing a core composition containing said at least 3 components (isotope C-labeled urea, excipient component and lubricant component) in tablet form and covering the surface of the core tablet with said coating agent. The core tablets can be produced by the granulation compression method (indirect compression method) which comprises blending the two components other than the lubricant component (namely, isotope C-labeled urea and excipient component), optionally together with other suitable additive components, granulating the mixture, adding the lubricant component, and compressing the whole mixture or the direct powder compression method (direct compression method) which comprises blending said 3 components, optionally together with other suitable additives, uniformly and directly compressing the whole mixture. Although whichever of said direct powder compression method and said granulation compression method can be used as mentioned above, the direct powder compression method is preferred because the granulating step can be dispensed with. The covering with the coating agent can be carried out in the conventional manner, for example by the method using a coating pan or the method using a fluid-bed coating equipment.

The coated preparation of the present invention is prepared in such a manner that it contains 10~300 mg, preferably 50~150 mg, of the active component isotope C-labeled urea per dosage unit.

The coated preparation of the present invention is useful for a test for *H. pylori* infection and for assessment of the bacterial elimination effect after eradication therapy. The procedure for detection or assessment is not particularly restricted but a typical protocol may comprise causing a test subject to ingest the coated preparation, e.g. a preparation containing 10~300 mg of $^{13}$C-labeled urea per dose unit, together with water in the fasted state, collecting expired air directly in a expired air bag after 5~60 minutes, preferably 10~20 minutes, and analyzing the same in a mass spectrometer for measurement of the $^{13}CO_2/^{12}CO_2$ ratio in the expired air.

EXAMPLES

The following reference and working examples illustrate the present invention in further detail but are by no means limitative of the scope of the invention.

Reference Example 1

The components indicated in Table 1 were blended in the indicated proportions and compressed by the direct compression method to prepare tablets of Reference Example 1. These tablets were tested as directed in Japanese Pharmacopeia (XIII), Dissolution Test [Method 2 (paddle method)] using water as the test solution at a bath temperature of 37±0.5° C. and a paddle speed of 50 rpm. The amount of dissolved urea (%) after 20 and 60 seconds were determined. The results are shown also in Table 1.

TABLE 1

| Core composition | Formulating amount |
|---|---|
| Urea | 100.0 mg |
| Lactose | 34.4 mg |
| Crystalline cellulose | 60.0 mg |
| Corn starch | 5.0 mg |
| Magnesium stearate | 0.6 mg |
| Amount of dissolved urea (after 20 sec), average | 3.1% |
| Amount of dissolved urea (after 60 sec), average | 46.6% |

The above results suggested that the dissolution of tablets of the formulation containing at least urea, an excipient component (lactose, crystalline cellulose, corn starch) and a lubricant (magnesium stearate) as tablet components is so rapid that when administered by the oral route, they dissolve quickly in the oral cavity.

Example 1

Tablets were manufactured according to the same formulation as used in Reference Example 1 except that an isotope ($^{13}$C)-labeled urea was used in lieu of urea. These core tablets were coated with an aqueous composition of hydroxypropylmethylcellulose/polyethylene glycol/titanium oxide/ talc (6/3/1/1, by weight) in a coating amount of 2 weight % based on 100 weight % of the core tablet by the coating method which is used generally in tablet manufacture to prepare coated tablets of the present invention. As in Reference Example 1, these coated tablets were tested in accordance with Japanese Pharmacopeia (XIII), Dissolution Test, Method 2 (paddle method), using water as the test solution at a bath temperature of 37±0.5° C. and a paddle speed of 50 rpm, and the amount of dissolved $^{13}$C-urea (%) after 20 and 60 seconds and 10 minutes were determined. The formulations used and dissolution test results are shown in Table 2.

TABLE 2

| | Formulation | Formulating amount |
|---|---|---|
| Core | $^{13}$C-urea | 100.0 mg |
| | Lactose | 34.4 mg |
| | Crystalline cellulose | 60.0 mg |
| | Corn starch | 5.0 mg |
| | Magnesium stearate | 0.6 mg |
| Coating | Hydroxypropylmethylcellulose | 2.4 mg |
| | Polyethylene glycol | 0.8 mg |
| | Titanium oxide | 0.4 mg |
| | Talc | 0.4 mg |
| Amount of dissolved urea (after 20 sec), average | | 0.0% |
| Amount of dissolved urea (after 60 sec), average | | 11.8% |
| Amount of dissolved urea (after 10 min), average | | 93.1% |

The above results indicate that the release of urea was not observed at 20 sec. following administration and was only slight at even 60 sec. It was, therefore, clear that as the coated tablet of the invention is swallowed together with water in the usual manner, the tablet finds its way into the stomach without dissolving in the oral cavity and releases the isotope-labeled urea in the stomach and that, therefore, a gastric *H. pylori* infection can be detected without being confounded by the urease present in the oral cavity.

Example 2

The proper amount of the coating agent relative to the core tablet by weight was explored based on the result of Example 1. Thus, coating solutions were prepared in coating-core weight ratios over the range of 0 to 20% (0, 0.1, 0.3, 0.5, 1, 2, 3, 5, 10, 15 and 20%) relative to 100 weight parts of the core tablet in the same manner as in Example 1 and the disintegration test was performed on each coated tablet to measure its lag time preceding disintegration and disintegration time. The core composition of the coated tablets used in the test are shown below.

| <Core> | |
|---|---|
| $^{13}$C-urea | 100.0 mg |
| Lactose (Dilactose S, Freund Ind.) | 34.4 mg |
| Crystalline cellulose (Avicel PH-101, Asahi Kasei) | 60.0 mg |
| Corn starch | 5.0 mg |
| Magnesium stearate | 0.6 mg |

Coated tablets containing 0.1~20 weight % of the coating agent based on 100 weight % of the above core were prepared by using coating solutions containing the following components in a coating amount of 1 or 8 weight %.

| <Coating solution> | |
|---|---|
| Hydroxypropylcellulose (TC-5RW, Shin-Etsu Chemical) | 6 wt. parts |
| Macrogol 6000 | 2 wt. parts |
| Titanium oxide | 1 wt. parts |
| Talc | 1 wt. parts |

(1) Measurement of Disintegration Time (Disintegration Test)

Each coated tablet prepared as above was tested as directed in Japanese Pharmacopoeia (XIII), Disintegration Test ["Tablets coated with suitable coating agents"] using water as the test solution and a bath temperature of 37±2° C., (6 test tablets). The time which elapsed until no residues of the test tablet were detected in the glass tube any longer or, if any residue was present, it was a filmy or spongy substance or only a soft or sludge-like substance was slightly detected was measured and recorded as disintegration time.

(2) Measurement of Lag Time (Dissolution Test)

Each coated tablet prepared above was tested as directed in Japanese Pharmacopoeia (XIII), Dissolution Test [Method 2 (paddle method)] using water (500 ml) as the test solution at a bath temperature of 37±0.5° C. and a paddle speed of 75 rpm, and the time from the start of paddle rotation to the start of tablet disintegration was measured and regarded as lag time.

The disintegration time and lag time data generated by the above tests with the coated tablets are shown in Table 3.

TABLE 3

| Coating amount | 0% | 0.1% | 0.3% | 0.5% | 1.0% | 2.0% |
|---|---|---|---|---|---|---|
| Disintegration time | 10"–15" | 10"–15" | 10"–15" | 10"–15" | 10"–15" | 10"–15" |
| Lag time | — | 5 sec. | 10–15 sec. | 15–20 sec. | 20–40 sec. | 20–40 sec. |

| Coating amount | 3.0% | 5.0% | 10.0% | 15.0% | 20.0% |
|---|---|---|---|---|---|
| Disintegration time | 15"–20" | 45"–55" | 1'55"–2'35" | 2'20"–3'10" | 3'30"–4'10" |
| Lag time | 20–40 sec. | 20–40 sec. | 1–2 min. | 2–3 min. | 3–4 min. |

The disintegration test revealed that while the coated preparations corresponding to the coating amounts of 0~3 weight % showed little variation In disintegration time, the coated preparation corresponding to the coating amount of 5 weight % showed slight retardation and, when the coating amount exceeded 10 weight %, it took 2 minutes or longer for the coated preparations to disintegrate. The dissolution test revealed that the start of release of the core composition could be retarded (induction of a lag time) by 0.1 weight % coating and that this lag time could be prolonged by increasing the coating amount to 0.3 weight % or more, preferably not less than 0.5 weight %. There was little difference in the lag time among the coated preparations over the coating amount range of 1~5 weight %. However, as the coating amount exceeded 10 weight %, the lag time was considerably prolonged, suggesting that the actual release of the core composition would be delayed. These findings suggested that the preferred proportion of the coating agent based on 100 weight % of the core composition is generally 0.1~10 weight %, more preferably 0.3~5 weight %, still more preferably 0.5~3 weight %, particularly 1~3 weight %.

Example 3

Using the coated preparation obtained in Example 1, the following experiment was performed.

Thus, by carrying out the $^{13}$C-labeled urea breath test using a solution of $^{13}$C-urea in adult men, 14 *H. pylori*-negative cases and 6 *H. pylori*-positive cases, or a total of 20 cases, were selected, and the following experiment was performed in these cases.

First, the above 20 cases were divided into two groups, Group A and Group B (each group: 7 *H. pylori*-negative and 3 *H. pylori*-positive cases) and the $^{13}$C-labeled urea breath test using the coated preparation of the invention was performed twice, 7 days apart, in each case. Thus, in Group A, mouth washing was carried out at the first breath test (mouth-washed) but not carried out at the second breath test (non-mouth-washed). In Group B, mouth washing was not carried out at the first breath test (non-mouth-washed) but carried out at the second breath test (mouth-washed).

The breath test was performed as follows. Each subject was instructed to ingest the coated preparation together with 100 mL of water and the expired air was collected into an aluminum-laminated bag of about 300 mL capacity at 6 points of time, namely before tablet intake and 5 min, 10 min, 15 min, 20 min, and 30 min after intake. The expired air thus collected was analyzed using an automatic $^{13}CO_2$ urea breath analyzer (GC-MS, tradename: ABCA-G (Europe Scientific)). Thus, for each expired air sample transferred from the aluminum-laminated bag to the exclusive reduced-pressure sampling tube, the $\delta\ ^{13}C$ value (‰) (the $^{13}CO_2/^{12}CO_2$ concentration ratio of the expired air at each sampling time) was determined. Then, the $\Delta\ ^{13}C$ value (‰), which is the difference between the $\delta\ ^{13}C$ value (‰) of the expired air sample before tablet intake and the $\delta\ ^{13}C$ value (‰) of the expired air at each sampling time after intake, was calculated.

The $\Delta\ ^{13}C$ value (‰) [the difference in the $^{13}CO_2/^{12}CO_2$ concentration ratio ($\delta\ ^{13}C$ value) of the expired air before tablet administration and the expired air at each sampling time after administration] was determined after oral administration in the respective test groups (the mouth-washed group and non-mouth-washed group each consisting of *H. pylori*-negative and *H. pylori*-positive cases) and the results are shown in FIG. 1. In FIG. 1, the closed circle represents the result for 14 *H. pylori*-negative cases (mouth-washed group), the open circle represents the result for 14 *H. pylori*-negative cases (non-mouth-washed group), the closed diamond represents the result for 6 *H. pylori*-positive cases (mouth-washed group), and the open diamond represents the result for 6 *H. pylori*-positive cases (non-mouth-washed group). Each graph shows the mean ± standard error for the total test population.

(1) Influence of Bacteria Resident in the Mouth and Throat

It is apparent from FIG. 1 showing the test results in *H. pylori*-negative cases (indicated by the closed circle and open circle on the drawing) that when the coated preparation of the present invention was used as a test reagent, omission of mouth washing did not introduce a change in $\Delta\ ^{13}C$ value that might be attributed to the influence of mouth and throat bacteria.

(2) The Time-Course Pattern of $\Delta\ ^{13}C$ Value (‰) in *H. pylori*-Positive Patients Whereas the $\Delta\ ^{13}C$ value (‰) reflecting the urease activity of *H. pylori* in the stomach could be detected in *H. pylori*-positive cases (indicated by the closed and open diamonds on the drawing), little change was found in the $\Delta\ ^{13}C$ value (‰) in *H. pylori*-negative cases (indicated by the closed and open circles on the drawing) as mentioned above. It was, therefore, evident that by using the coated preparation of the present invention as a diagnostic reagent, the $\Delta\ ^{13}C$ value (‰) in a *H. pylori*-positive case and the $\Delta\ ^{13}C$ value (‰) in a *H. pylori*-negative case can be detected with a clear distinction, hence a *H. pylori*-positive patient and a *H. pylori*-negative patient can be accurately sorted out, that is to say a *H. pylori* infection can be accurately diagnosed.

It was confirmed from the above results that by covering the uncoated tablet (core tablet) containing $^{13}$C-labeled urea and other components with the coating agent at the defined coating rate, the influence of the urease-producing bacteria in the mouth and throat can be completely excluded, thus permitting an accurate diagnosis of a *H. pylori* infection.

INDUSTRIAL APPLICABILITY

The conventional diagnostic reagent for *H. pylori* infection gives false-positive results at times, for because the reagent powder of isotope C-labeled urea is dissolved in water and administered in the form of an aqueous solution, the test result tends to be confounded by the urease-producing bacteria in the mouth and throat. Therefore, in order that an accurate determination may be made, it is necessary to have the mouth washed immediately after administration of the labeled urea-containing solution or perform a determination on the expired air collected at least 20 minutes after ingestion by which time the influence of the resident bacteria in the oral cavity may have diminished, among other restrictions.

With the coated preparation of the present invention, the influence of the urease-producing bacteria resident in the mouth and throat is completely excluded so that the test is not subject to the above restrictions. Moreover, since the dissolution and dispersion of the active component in the stomach are rapid, it is possible to collect expired air early after ingestion and measure the labeled carbon dioxide to make a rapid determination of *H. pylori* infection. Furthermore, exclusion of the influence of oral bacteria means that the cut-off value as a criterion of *H. pylori* infection can be set more stringent and low to thereby further improve the detection accuracy and reduce the time required for determination. Therefore, the coated preparation of the present invention is considered to be a very useful preparation for use as a diagnostic reagent for *H. pylori* infection yielding more rapid, expedient and accurate test results.

The invention claimed is:

1. A coated preparation product for use in the detection of *Helicobacter pylori* infection comprising:
   (i) a core composition comprising:
   about 19 to about 89 parts by weight of isotope carbon-labeled urea relative to 100 parts by weight of the core composition,
   about 10 to about 80 parts by weight of an excipient component relative to 100 parts by weight of the core composition, and
   about 0.01 to about 1 parts by weight of a lubricant component relative to 100 parts by weight of the core composition;
   the excipient component comprising:

(a) at least one member selected from the group consisting of lactose, sucrose, and glucose,
(b) at least one member selected from the group consisting of crystalline cellulose, low-substitution hydroxypropyl cellulose, carboxymethylcellulose calcium, and croscarmellose sodium, and,
(c) at least one member selected from the group consisting of starch, carboxymethylstarch sodium, hydroxypropylstarch, and partially pregelatinized starch; and
(ii) a coating agent;
the core composition being coated with about 0.1 to about 5 parts by weight of the coating agent relative to 100 parts by weight of the core composition.

2. A coated preparation according to claim 1, wherein the amount of the coating agent ranges from about 0.3 to about 5 parts by weight relative to 100 parts by weight of the core composition.

3. A coated preparation according to claim 1, wherein the amount of the coating agent ranges from about 0.3 to about 3 parts by weight relative to 100 parts by weight of the core composition.

4. A coated preparation according to claim 1 containing:
from about 25 to about 75 parts by weight of the isotope carbon-labeled urea relative to 100 parts by weight of the core composition,
from about 20 to about 70 parts by weight of the excipient component relative to 100 parts by weight of the core composition, and
from about 0.05 to about 0.8 parts by weight of the lubricant component relative to 100 parts by weight of the core composition.

5. A coated preparation according to claim 1 containing:
from about 30 to about 70 parts by weight of the isotope carbon-labeled urea relative to 100 parts by weight of the core composition,
from about 35 to about 65 parts by weight of the excipient component relative to 100 parts by weight of the core composition, and
from about 0.1 to about 0.7 parts by weight of the lubricant component relative to 100 parts by weight of the core composition.

6. A coated preparation according to claim 1, wherein the core composition contains:
from about 10 to about 450 parts by weight of the excipient component relative to 100 parts by weight of the isotope carbon-labeled urea, and
from about 0.01 to about 6 parts by weight of the lubricant component relative to 100 parts by weight of the isotope carbon-labeled urea.

7. A coated preparation according to claim 1, wherein the core composition contains:
from about 50 to about 150 parts by weight of the excipient component relative to 100 parts by weight of the isotope carbon-labeled urea, and
from about 0.1 to about 5 parts by weight of the lubricant component relative to 100 parts by weight of the isotope carbon-labeled urea.

8. A coated preparation according to claim 1, wherein the coating agent comprises a water-soluble polymer and a plasticizer.

9. A coated preparation according to claim 8 wherein the water-soluble polymer is at least one member selected from the group consisting of pullulan, dextrin, alkali metal alginate, hydroxypropylcellulose, hydroxypropylmethylcellulose, methylcellulose and polyvinylpyrrolidone.

10. A coated preparation according to claim 8 wherein the plasticizer is at least one member selected from the group consisting of polyvinyl alcohol, polyethylene glycol, triethyl citrate, triacetin, concentrated glycerin, propylene glycol and polysorbate.

11. A coated preparation according to claim 1 wherein, as the lubricant component, the core composition contains at least one member selected from the group consisting of stearic acid, magnesium stearate, calcium stearate and hydrogenated oil.

12. A coated preparation according to claim 1 wherein the core composition contains lactose, crystalline cellulose and starch as the excipient component and magnesium stearate as the lubricant component and the coating agent contains hydroxypropylmethylcellulose, polyethylene glycol, titanium oxide and talc.

13. A coated preparation according to claim 1 wherein the isotope carbon-labeled urea is $^{13}$C-labeled urea.

14. The coated preparation according to claim 1 wherein the excipient component comprises lactose, crystalline cellulose and starch.

15. The coated preparation according to claim 1, wherein the saccharide is at least one member selected from the group consisting of lactose, sucrose, and glucose.

* * * * *